US008148582B2

(12) United States Patent
Dubois

(10) Patent No.: US 8,148,582 B2
(45) Date of Patent: Apr. 3, 2012

(54) GLYCEROL VAPORIZATION METHOD

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 220 days.

(21) Appl. No.: 12/530,972

(22) PCT Filed: Mar. 14, 2008

(86) PCT No.: PCT/FR2008/050438
§ 371 (c)(1),
(2), (4) Date: Feb. 26, 2010

(87) PCT Pub. No.: WO2008/129208
PCT Pub. Date: Oct. 30, 2008

(65) Prior Publication Data
US 2010/0230635 A1     Sep. 16, 2010

(30) Foreign Application Priority Data
Mar. 19, 2007 (FR) ..................................... 07 53896

(51) Int. Cl.
*C07C 29/76* (2006.01)
*C07C 29/94* (2006.01)

(52) U.S. Cl. ...................................................... 568/869

(58) Field of Classification Search .................... 568/869
See application file for complete search history.

(56) References Cited

FOREIGN PATENT DOCUMENTS

| FR | 2753293 | 3/1933 |
|---|---|---|
| WO | WO 2006087083 | 8/2006 |
| WO | WO 2006087084 | 8/2006 |
| WO | WO 2006114506 | 11/2006 |
| WO | WO 2007090990 | 8/2007 |

OTHER PUBLICATIONS

Anderson, et al; "*Glycerine Recovery from Spent Lyes and Sweetwater*"; Crown Iron Works Company; Chapter 5; pp. 172-207.
D'Souza; "*The Importance of Glycerol in the Fatty Acid Industry*"; Am. Oil Chemists' Soc. Nov. 1979: vol. 56, p. 812A.
Schaffner; "*Electrodialysis of Crude Glycerin Recovered After Esterification of Colza Oil*"; The British Library—"The world's knowledge"; pp. 629-633.
Steinberner, et al: *Glcerin-Ein fettchemischer Grundstoff im Wandel der Zaif*: Fat. Sci. Technol.; 89. Jahrgang No. 8 1987; pp. 297-303.

*Primary Examiner* — Elvis O Price
(74) *Attorney, Agent, or Firm* — Hunton & Williams LLP

(57) ABSTRACT

The subject matter of the present invention relates to a vaporization method of aqueous glycerol solutions in a fluidized bed containing an inert solid. The invention provides a method for vaporizing, in a single step, an aqueous glycerol solution and simultaneously eliminating the impurities present in this solution or generated during the evaporation.

7 Claims, 1 Drawing Sheet

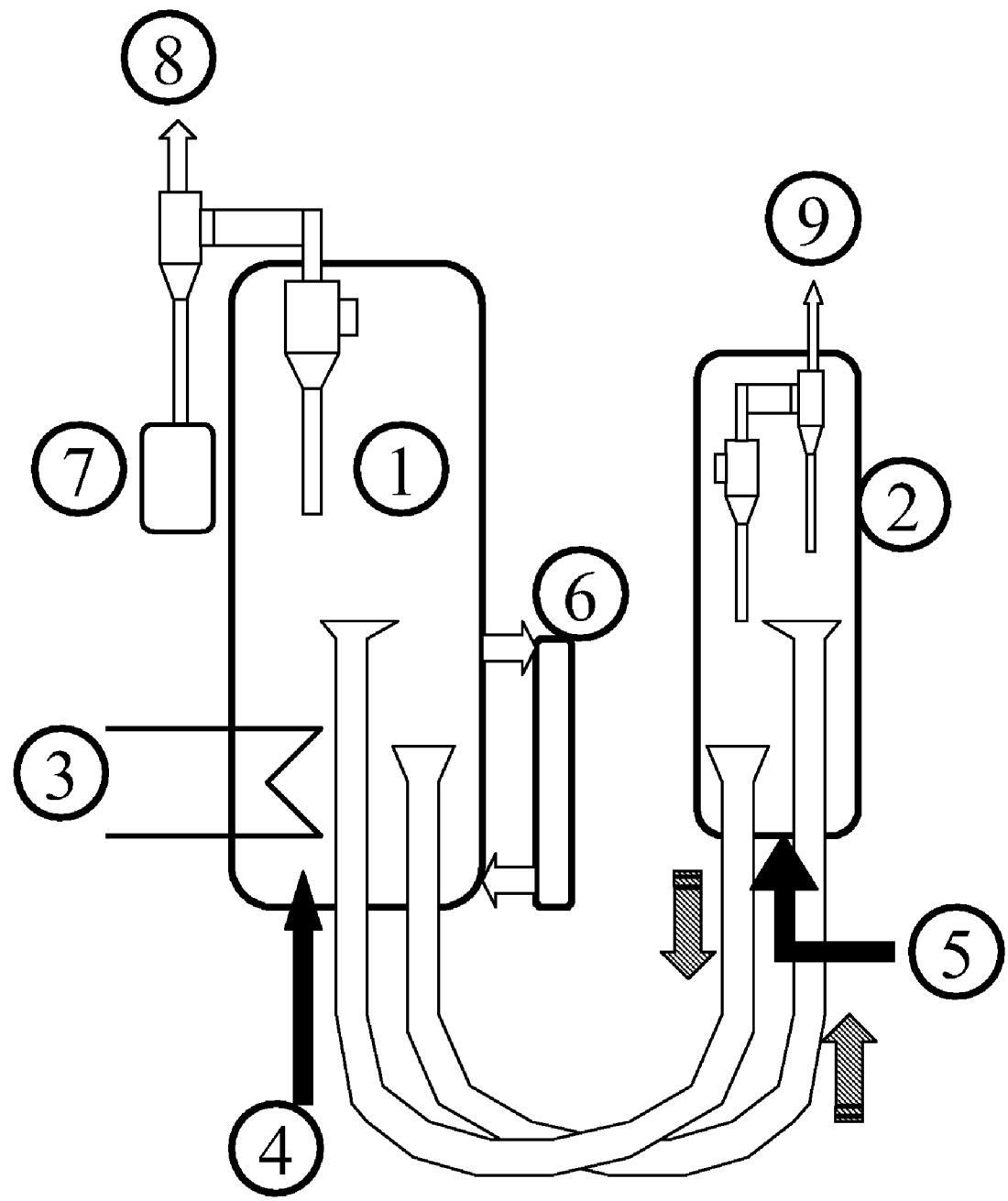

GLYCEROL VAPORIZATION METHOD

CROSS-REFERENCE TO RELATED APPLICATIONS

This application is the U.S. National Phase of International Application No. PCT/FR2008/050438, filed Mar. 14, 2008, which claims the benefit of French Application No. FR 0753896, filed Mar. 19, 2007, the disclosure of each of which is incorporated herein by reference in its entirety.

FIELD OF THE INVENTION

One object of the present invention is a method of vaporizing aqueous solutions of glycerol in a fluidized bed containing an inert solid, that makes it possible to simultaneously remove the impurities present in these solutions or that are generated during the evaporation.

BACKGROUND

Glycerol is a chemical, 1,2,3-propanetriol, which may be obtained either by chemical synthesis from propylene, or as a by-product formed during the methanolysis of vegetable oils.

The methanolysis of vegetable oils may be carried out according to various processes, in particular by using a homogeneous catalyst such as sodium hydroxide or sodium methylate in solution in methanol, or by using a heterogenous catalyst. Reference may be made, on this subject, to the article by D. Ballerini et al. in L'Actualité Chimique of November-December 2002.

The methanolysis of vegetable oils results, on the one hand, in methyl esters, and on the other hand in glycerol. Methyl esters are used in particular as fuels or combustibles in diesel fuel and domestic fuel. With the development of fuels of renewable origins, and especially of vegetable oil methyl esters (VOMEs), the production of glycerol in accordance with this production method increases greatly, glycerol representing around 10% by weight of the oil converted.

Glycerol derived from vegetable oils is a natural product of renewable origin which is thus increasingly available. In the current context of the novel concept of green chemistry, and more generally of sustainable development, it is becoming increasingly advantageous to utilize this product.

However, the methods for producing VOMEs result in a glycerol that is more or less pure and more or less dilute in water. Generally, it is these more or less pure aqueous solutions of glycerol that are known as glycerin, according to the definition adopted by "The Soap and Detergent Association" (Soaps and Detergents: A theoretical and Practical Review, Miami Beach Fla., Oct. 12-14, 1994, chapter 6 pp. 172-206. Ed: L Spitz, AOCS Press, Champaign). Crude glycerin generally has a composition of the order of 88% glycerol, 9-10% water and 2-3% impurities. In particular, it may contain impurities such as basic salts (for example of sodium or of potassium), non-glycerin organic compounds, methanol or residues of vegetables oils. In certain applications of glycerol, the presence of these impurities is particularly prejudicial for the reactions carried out or for the quality of the finished products. For example, in the case of the production of acrolein, the presence of sodium or potassium salts is prejudicial for the catalytic dehydration reaction of glycerol to acrolein, as these salts are capable of poisoning the acid sites of the catalysts used.

Consequently, the aqueous solutions of crude glycerol or glycerin generally require a pretreatment before use, or a purification treatment in order to envisage novel applications.

Furthermore, it is often necessary not only to remove the impurities that are undesirable for the envisaged application, but also to concentrate the aqueous solution, or even to vaporize the aqueous solution, certain industrial processes using glycerol in vapor form. These operations are tricky as it is known that glycerol may decompose, in particular to acrolein, or result in polymers such as polyglycerol.

Various technologies for purifying glycerol have been described in the literature. Specifically, it is a product that has more than 1500 different applications, all requiring particular qualities, in particular there is a "Pharmacopeia" grade that requires a high purity of the glycerol.

Among the methods used or studied for the purification and evaporation of glycerol, mention will especially be made of those that are described by G. B. D'Souza, in J. Am. Oil Chemists' Soc. November 1979 (Vol 56) 812A, by Steinberner U et al., in Fat. Sci. Technol. (1987), 89 Jahrgang No. 8, pp. 297-303, and by Anderson D. D. et al. in Soaps and Detergents: A theoretical and Practical Review, Miami Beach Fla., Oct. 12-14, 1994, chapter 6, pp. 172-206. Ed: L Spitz, AOCS Press, Champaign.

The treatments of crude glycerol solutions proposed target the removal of the dissolved salts and of the organic impurities resulting from fatty substances, the removal of the color, an increase in the glycerol content, or the vaporization of the glycerol, depending on the final application envisaged.

In particular, in order to achieve these objectives, an evaporation, a distillation, a treatment with lime (in order to neutralize the residual fatty acids) followed by a filtration, an ion exchange or ion exclusion treatment, a separation by reverse osmosis or an electrodialysis may be carried out.

Multiple-effect evaporators are, for example, used for concentrating dilute solutions of glycerol. With a triple-effect evaporator, it is thus possible to evaporate 2.4 kg of water with 1 kg of steam.

Distillation is one of the techniques used for concentrating and purifying glycerin. As glycerol begins to decompose at around 202° C., i.e. well below its boiling point (293° C.), it is necessary to distil glycerin in several steps using reduced pressure. In certain cases, the distillation is carried out via batch operations, until the salts and the non-volatile compounds have accumulated sufficiently in the vessel. The operation is then stopped and the impurities are discharged from the vessel before restarting the distillation. The evaporation is carried out under vacuum, and the partial condensation of glycerol (which will condense before water) at the outlet of the unit makes it possible to directly obtain a concentrated glycerol. Typically, pressures of 10 mm Hg are used, for a temperature of 160-165° C., which gives low partial pressures of glycerol in the vapor phase.

The distilled glycerin still contains colored compounds. It is sometimes necessary to decolorize the glycerin for pharmaceutical and food applications. Typically activated carbon is added to the glycerin in order to decolorize it.

The purification of glycerin by ion exclusion has also been developed and uses ion resins in order to separate the ionic salts that are soluble in aqueous solution from non-ionic compounds such as glycerol. This is a technique which avoids the consumption of heat and of chemical regenerants, and which makes it possible to purify highly contaminated streams such as crude glycerin, using only water as a chemical regenerant.

Aqueous solutions of glycerol that are weakly contaminated by salts may be exchanged simply over acid and basic resins. The thus purified glycerol solutions may then be concentrated by evaporation.

The technique of reverse osmosis, based on a separation over a semi-permeable membrane by applying a pressure has been proposed for the concentration of particularly dilute glycerol streams.

Solutions of glycerin and of sodium hydroxide in methanol obtained after transesterification of rapeseed oil have been demineralized by membrane electrodialysis to produce pure glycerin. This technique is described in the reference: Schaffner, F. et al., Proc.—World Filtr. Congr. 7th, Volume 2, 629-633.

In the methods proposed for evaporating aqueous solutions of glycerol, the control of the temperature is very critical as certain undesirable reactions may take place, such as the formation of nitrogen-containing compounds by a degradation of protein matter present in the glycerin, the formation of a volatile glycerin ester by reaction with soaps of low molar mass, the formation of polyglycerol, the formation of acrolein which contributes to the odors of the final product. It is therefore important to limit the residence time of the glycerin at high temperature, and also this temperature. The evaporation processes used conventionally do not therefore make it possible to have high partial pressures of glycerol in the vapor phase. Furthermore, it is often necessary to combine several treatments in order to obtain the glycerol with a purity and at a concentration that are suitable for the envisaged application.

SUMMARY OF THE INVENTION

The applicant company has now surprisingly discovered a single-step process that makes it possible to vaporize an aqueous solution of glycerol and to simultaneously remove the impurities present, or generated in the course of the evaporation, in this solution.

The subject of the present invention is therefore a method of vaporizing aqueous solutions of glycerol (or glycerin) in a fluidized bed containing an inert solid.

DETAILED DESCRIPTION OF PREFERRED EMBODIMENTS

According to the method of the invention, the aqueous solution is injected directly into a fluidized bed containing an inert solid maintained at a sufficient temperature to allow the instantaneous vaporization of glycerol and of water.

As inert solids, use may be made, for example, of sand, of glass or quartz powder, of silicon carbide, or of solids having a low specific surface area, the solids of low specific surface area being, by nature, reputed to be inert, they may be composed of alumina, silica or silica-alumina. It will not be outside the scope of the invention to use, as an inert solid, a mineral salt, such as sodium chloride (NaCl), potassium chloride (KCl), sodium sulfate ($Na_2SO_4$) or potassium sulfate ($K_2SO_4$). Preferably, the inert solid is chosen from sand, silica, quartz or silicon carbide.

Fluidization may be provided by the vaporization of the glycerol solution, and/or by a stream of inert gas (nitrogen, $CO_2$, recycle gas, etc.), or of air, of oxygen, or a mixture of gases.

The temperature of the fluidized bed is generally between 220 and 350° C., preferably 260 to 320° C.

Other features and advantages of the invention will emerge more clearly on reading the description which follows and with reference to the single appended FIGURE.

The method according to the invention leads to high partial pressures of glycerol in the vapor phase, which has the advantage of vaporizing the glycerol with a substantially higher productivity than that obtained with vacuum distillation.

In the method according to the invention, the impurities present in the aqueous solution are removed simultaneously, as the fluidized bed technique makes it possible to continuously draw off a portion of the solid in order to regenerate it ex-situ. Thus, the organic compounds present in the glycerol solution and also the products resulting from the decomposition of the glycerol during this evaporation step, may result in the formation of coke which is deposited on the inert solid. When the aqueous glycerol solution contains salts (for example sodium chloride or sodium sulfate) these salts are also deposited on the inert solid during the evaporation of the aqueous glycerol solution. The inert solid comprising the coke and/or the mineral salts may then be drawn off continuously in order to be regenerated in another reactor, before being sent back into the fluidized bed. The removal of the mineral salts may be carried out by simple washing of the solid with water, or any other suitable technique. The regeneration of the solid consists of a combustion of the solid deposits, it is generally carried out with air in a reactor which may be, for example, another continuously operated fluidized bed, a fixed bed, or any other reactor which may be suitable. Preferably, use will be made of a continuously operated fluidized bed. The combustion of the carbonaceous deposits on the inert solid make it possible not only to regenerate it but also to reheat it before returning it to the fluidized bed for evaporation of glycerol. This combustion may be carried out in the presence of a fuel, for example methane, which helps to bring the inert solid to the temperature needed for the evaporation of the aqueous glycerol solution.

Furthermore, in a fluidized bed, the particles are moving relative to one another which causes an attrition of the solid. In conventional fluidized beds, it is sought to limit this attrition which consumes the solid and produces fine particles. In the process according to the invention, the attrition makes it possible to remove a portion of the deposits which are formed on the inert solid. The fine particles thus formed by attrition are removed downstream, for example by separation in a cyclone or by filtration.

In one embodiment of the method according to the invention, represented in the single FIGURE, an aqueous solution of glycerol or of glycerin (4) is introduced into a reactor (1) containing a fluidized bed of an inert solid. The fluidization may optionally be provided by a stream of inert gas (nitrogen, $CO_2$, recycle gas, etc.), or of air, of oxygen, or of a mixture of gases which may be chosen so that the composition of 8 corresponds as best possible to the feed for the downstream processes. The fluidized bed is heated via the heat exchanger (3). The glycerol and water vapors are extracted from the reactor at (8) and a unit (7) makes it possible to recover the fine particles from the installation. A unit (6) makes it possible to wash the solid used in the fluidized bed in order to remove the mineral salts deposited. The reactor (2) is a regenerator of the inert solid in which the solid drawn off from (1) is subjected to a combustion in the presence of a regeneration gas (5) containing molecular oxygen and/or fuels, the regenerated solid being sent back to the reactor (1). The gases resulting from the regeneration unit are discharged at (9).

The glycerol vapors obtained according to this method can then be used directly in a downstream process that uses glycerol in gas form, such as for example the processes for producing acrolein or acrylic acid described in documents WO 06/087083, WO 06/087084, WO 06/114506, WO 07/090,990 and WO 07/090,991, or a process for producing acrylonitrile as described in Application FR 07/53293. They may also be condensed making it possible to produce concentrated and purified aqueous glycerol solutions.

The invention also relates to the use of a fluidized bed containing an inert solid in order to vaporize and purify aqueous glycerol solutions.

The present invention will now be described in the examples below, such examples being given in a uniquely illustrative and obviously non-limiting manner.

Examples 150 g of silica having the particle size of 100 μm was placed in a fluidized bed. The fluidized bed consists of a stainless steel tube having a diameter of 41 mm and a total height of 790 mm. The fluidized bed is immersed in a bath of fluidized sand, heated by electrical elements installed inside the bath. Three thermocouples recorded the temperature gradient along the tube. Air was supplied at a flow rate of 500 ml/min (standard conditions), underneath a porous metal plate that distributes the gas across the diameter of the reactor. The solution to be tested/nitrogen mixture is supplied by a 0.6 mm metal tube that goes up to the base of the bed with a mass flow rate of 0.5 g/min, while maintaining the nitrogen flow rate at 1000 ml/min. The total pressure in the fluidized bed is 1.2 bar and the temperature is maintained at 310° C.

The experiment was carried out with an aqueous solution containing 18% by weight of pure glycerol (99.5% Laboratoire MAT) and 2% by weight of NaCl salt over 60 min, which corresponds to a total mass of 0.6 g of salt supplied at the entry of the fluidized bed.

The products are collected at the exit from the fluidized bed and condensed in order to be analyzed by conductivity.

The conductivity measurement was carried out on an Accumet Research AR-20 pH meter/conductivity meter type device. The results are collated in the table below.

| Solution | Conductivity microS/cm |
|---|---|
| Pure glycerol | 9 |
| Distilled water | 5 |
| Aqueous solution containing 18% of pure glycerol and 2% of salt | 4650 |
| Solution collected in the condenser at the outlet of the fluidized bed | 15 |

The total mass of salt recovered in the condenser is 0.0004 g, which corresponds to a 99.9% efficiency for the separation of the salt in the fluidized bed, expressed by the low conductivity of the solution collected in the condenser.

The invention claimed is:

1. A method comprising:
   vaporizing an aqueous solution of glycerol in a fluidized bed comprising an inert solid maintained at a temperature ranging from 220 to 350° C.

2. The method of claim 1, wherein the inert solid comprises sand, glass or quartz powder, silicon carbide, a solid having a low specific surface area, or mixtures thereof.

3. The method of claim 1, wherein the inert solid is regenerated in a second continuously operated fluidized bed.

4. The method of claim 2, wherein the inert solid is regenerated in a second continuously operated fluidized bed.

5. The method of claim 1, wherein said aqueous solution of glycerol is purified by said vaporizing.

6. The method of claim 1, wherein said vaporizing occurs in a single step of injecting said aqueous solution of glycerol into the fluidized bed.

7. A method comprising:
   vaporizing and purifying an aqueous solution of glycerol in a single step comprising injecting said solution into a fluidized bed comprising an inert solid.

* * * * *